(12) United States Patent
Evans et al.

(10) Patent No.: US 9,755,024 B2
(45) Date of Patent: Sep. 5, 2017

(54) FUNCTIONALIZED ZNO OR ZNO ALLOY FILMS EXHIBITING HIGH ELECTRON MOBILITY

(71) Applicant: Wisconsin Alumni Research Foundation, Madison, WI (US)

(72) Inventors: Paul G. Evans, Madison, WI (US); Josef W. Spalenka, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 652 days.

(21) Appl. No.: 14/161,819

(22) Filed: Jan. 23, 2014

(65) Prior Publication Data
US 2014/0203826 A1 Jul. 24, 2014

Related U.S. Application Data

(60) Provisional application No. 61/756,069, filed on Jan. 24, 2013.

(51) Int. Cl.
| | | |
|---|---|---|
| *H01L 29/08* | (2006.01) |
| *H01L 35/24* | (2006.01) |
| *H01L 51/00* | (2006.01) |
| *H01L 29/24* | (2006.01) |
| *H01L 29/786* | (2006.01) |
| *H01L 27/12* | (2006.01) |
| *G01N 27/414* | (2006.01) |

(52) U.S. Cl.
CPC ......... *H01L 29/24* (2013.01); *G01N 27/4146* (2013.01); *H01L 27/1222* (2013.01); *H01L 29/7869* (2013.01); *H01L 29/78606* (2013.01)

(58) Field of Classification Search
CPC ........... H01L 29/7869; H01L 29/78606; H01L 29/24; G01N 27/414; G01N 27/4148; G01N 27/4145; G01N 33/48785; G01N 33/48707; B82Y 35/00
See application file for complete search history.

(56) References Cited

U.S. PATENT DOCUMENTS

| | | | |
|---|---|---|---|
| 9,064,965 B2 * | 6/2015 | Lu ........................ H01L 29/7869 |
| 2002/0167003 A1 * | 11/2002 | Campbell ............... B82Y 15/00 |
| | | | 257/40 |
| 2004/0127038 A1 * | 7/2004 | Carcia ................... C23C 14/086 |
| | | | 438/689 |

(Continued)

OTHER PUBLICATIONS

Changshi Lao et al., "Enhancing the Electrical and Optoelectronic Performance of Nanobelt Devices by Molecular Surface FUnctionalization", 2007, Nano Letters, vol. 7, No. 5, p. 1323-1328.*

(Continued)

*Primary Examiner* — Jesse Y Miyoshi
(74) *Attorney, Agent, or Firm* — Bell & Manning, LLC

(57) ABSTRACT

Functionalized films are provided comprising a film of ZnO or ZnO alloy disposed over a supporting substrate and a layer of organic molecules comprising terminal carboxylic acid linkage groups, wherein the organic molecules are bound to a surface of the film of ZnO or ZnO alloy via the terminal carboxylic acid linkage groups. Thin film transistors comprising the functionalized films are also provided. The functionalized films may be formed using polycrystalline ZnO and saturated fatty acids, such as stearic acid.

18 Claims, 6 Drawing Sheets

(56) References Cited

U.S. PATENT DOCUMENTS

2005/0227405 A1* 10/2005 Sudholter ............ G01N 27/414
438/99
2012/0090684 A1 4/2012 Yang et al.

OTHER PUBLICATIONS

Kwak et al., Superhydrophobic ZnO Nanowire Surface: Chemical Modification and Effects of UV Irradiation, J. Phys. Chem. C, vol. 113, Jun. 12, 2009, pp. 12085-12089.

Badre et al., A ZnO nanowire array film with stable highly water-repellent properties, Nanotechnology, vol. 18, No. 365705, Aug. 10, 2007, pp. 1-4.

Eichberger et al., Charge separation dynamics at inorganic/organic nanostructured hybrid photovoltaic interfaces, Journal of Photonics for Energy, vol. 2, Mar. 12, 2012, pp. 021003-1-021003-8.

McNamara et al., Acetylacetonate Anchors for Robust Functionalization of TiO2 Nanoparticles with Mn(II)-Terpyridine Complexes, J. Am. Chem. Soc., vol. 130, Oct. 3, 2008, pp. 14329-14338.

Carter et al., Small molecule chemisorption on indium-tin oxide surfaces: enhancing probe molecule electron-transfer rates and the performance of organic light-emitting diodes., J Phys Chem B., vol. 110, No. 50, 2006, pp. 25191-25202.

Armstrong et al., Interface modification of ITO thin films: organic photovoltaic cells, Thin Solid Films, vol. 445, 2003, pp. 342-352.

Liu et al., Surface Functionalization of ZnO Nanotetrapods with Photoactive and Electroactive Organic Monolayers, Langmuir, vol. 24, Mar. 28, 2008, pp. 5052-5059.

Lao et al., Enhancing the Electrical and Optoelectronic Performance of Nanobelt Devices by Molecular Surface Functionalization, Nano Letters, vol. 7, No. 5, Mar. 31, 2007, pp. 1323-1328.

Spalenka et al., Molecular control of pentacene/ZnO photoinduced charge transfer, Applied Physics Letters, vol. 98, No. 103303, Mar. 9, 2011, pp. 1-3.

Allen et al., Alkyl Surface Treatments of Planar Zinc Oxide in Hybrid Organic-Inorganic Solar Cells, The Journal of Physical Chemistry C, vol. 116, No. 16, Apr. 10, 2012, pp. 8872-8880.

Spalenka et al., Spectral resolution of states relevant to photoinduced charge transfer in modified pentacene/ZnO field-effect transistors, Applied Physics Letters, vol. 99, No. 193304, Nov. 9, 2011, pp. 1-3.

Allen et al., Surface Modification of ZnO Using Triethoxysilane-Based Molecules, Langmuir, vol. 24, No. 23, Oct. 30, 2008, pp. 13393-13398.

Monson et al., Photocurrent Enhancement in Polythiophene- and Alkanethiol-Modified ZnO Solar Cells, Advanced Materials, vol. 20, No. 24, Nov. 27, 2008, pp. 4755-4759.

Pan et al., Nanobelts of Semiconducting Oxides, Science, vol. 291, Mar. 9, 2001, pp. 1947-1949.

Spalenka et al., Electron mobility enhancement in ZnO thin films via surface modification by carboxylic acids, Applied Physics Letters, vol. 102, No. 041602, Jan. 29, 2013, pp. 1-5.

Spalenka et al., Field-Effect Transistor Probes of Charge-Transfer in Donor-Sensitized ZnO Interfaces, poster presentation at MRS Conference, Nov. 28, 2012.

Spalenka et al., Field-Effect Transistor Probes of Charge-Transfer in Donor-Sensitized ZnO Interfaces, abstract for MRS Conference, Aug. 20, 2012.

* cited by examiner

FUNCTIONALIZED ZNO OR ZNO ALLOY FILMS EXHIBITING HIGH ELECTRON MOBILITY

CROSS-REFERENCE TO RELATED APPLICATIONS

The present application claims priority to U.S. Provisional Patent Application No. 61/756,069 that was filed Jan. 24, 2013, the entire content of which is hereby incorporated by reference.

REFERENCE TO GOVERNMENT RIGHTS

This invention was made with government support under 1121288 awarded by the National Science Foundation. The government has certain rights in the invention.

BACKGROUND

ZnO is an inorganic semiconductor with applications in large-area photovoltaics and transparent electronics. Producing ZnO thin films with excellent electronic properties is challenging and has required a series of processing tools including vacuum deposition techniques, such as rf magnetron sputtering, and post-deposition annealing in controlled gas environments. ZnO thin films can be produced from solution-deposited precursors, enabling new technologies such as printing of electronic circuits and deposition in continuous industrial processes rather than batch processes. However, since such films are dominated by defects and impurities, the electronic properties of these films must be enhanced via subsequent processing steps. Common strategies include high-temperature annealing in either hydrogen gas environments or in the presence of a hydrogen-rich capping layer, which increases the carrier concentration by introducing hydrogen into the ZnO and creates shallow donor states. Removing oxygen-vacancy donor states by annealing in an oxygen-rich environment has the opposite effect, reducing the carrier concentration. The high-temperature processing steps typically involve temperatures at 350-600° C.

SUMMARY

Provided herein are functionalized ZnO or ZnO alloy films and related devices. Also provided are methods for forming the films and methods for using the devices.

In one aspect, a functionalized film is provided comprising a film of polycrystalline ZnO or alloy thereof disposed over a supporting substrate and a layer of organic molecules comprising terminal carboxylic acid linkage groups, wherein the organic molecules are bound to a surface of the film of polycrystalline ZnO or alloy thereof via the terminal carboxylic acid linkage groups.

In another aspect, a thin film transistor is provided comprising a layer of a gate material; a layer of a dielectric material disposed over and in contact with the layer of the gate material; a functionalized film disposed over and in contact with the layer of the dielectric material; a source disposed over the layer of the dielectric material and in contact with the functionalized film at a first interface; and a drain disposed over the layer of the dielectric material and in contact with the functionalized film at a second interface. The functionalized film comprises a film of polycrystalline ZnO or alloy thereof, and a layer of organic molecules comprising terminal carboxylic acid linkage groups, wherein the organic molecules are bound to a surface of the film of polycrystalline ZnO or alloy thereof via the terminal carboxylic acid linkage groups.

In another aspect, a sensor for detecting carboxylic acid-containing molecules in a sample is provided comprising a layer of a gate material; a layer of a dielectric material disposed over and in contact with the layer of the gate material; a polycrystalline ZnO or ZnO alloy film disposed over and in contact with the layer of the dielectric material; a source disposed over the layer of the dielectric material and in contact with the polycrystalline ZnO or ZnO alloy film at a first interface; a drain disposed over the layer of the dielectric material and in contact with the polycrystalline ZnO or ZnO alloy film at a second interface; and a device configured to measure the conductivity or electron mobility of the polycrystalline ZnO or ZnO alloy film in the presence of a sample in contact with the polycrystalline ZnO or ZnO alloy film and further configured to indicate the presence or absence of carboxylic acid-containing molecules in the sample from the measured conductivity or electron mobility.

In another aspect, a method of detecting carboxylic acid-containing molecules in a sample is provided comprising exposing the polycrystalline ZnO or ZnO alloy film of the sensor described above to a sample; and measuring the conductivity or electron mobility of the polycrystalline ZnO or ZnO alloy film, whereby the measured conductivity or electron mobility indicates the presence or absence of carboxylic acid-containing molecules in the sample.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
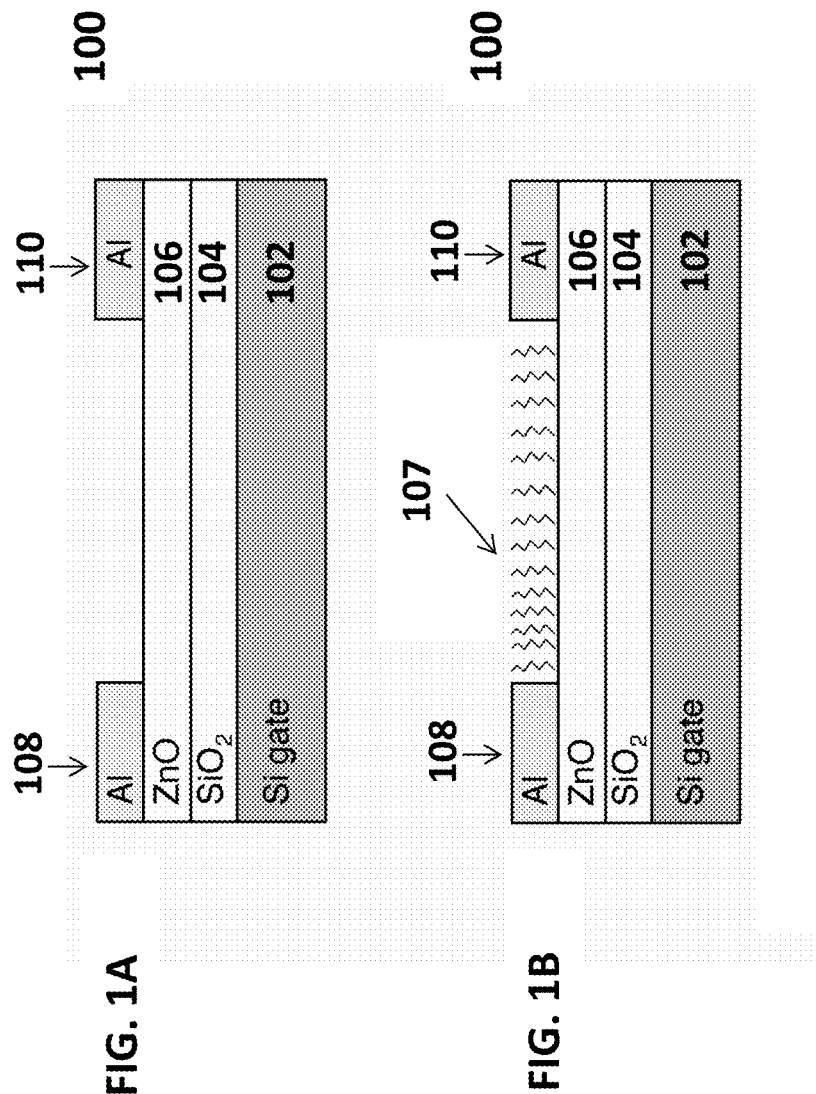
FIG. 1 depicts a schematic illustration of a field-effect transistor (FET) comprising an unfunctionalized ZnO film (A) and the FET after functionalization of the ZnO film with stearic acid (B).

Provided herein are functionalized ZnO or ZnO alloy films and devices incorporating the functionalized films. Also provided are methods for forming the films and methods for using the devices.

In at least some embodiments, the ZnO or ZnO alloy films to be functionalized have been deposited using solution-based methods (e.g., sol-gel processes, chemical bath deposition and decomposition of low-temperature inorganic inks), rather than using vacuum-based methods (e.g., sputtering). However, in other embodiments, the ZnO or ZnO alloy films to be functionalized have been deposited using vacuum-based methods. Under many conditions, especially at thicknesses of less than 100 nm, as-deposited ZnO or ZnO alloy films may exhibit electronic properties that limit the utility of such films in electronic and optoelectronic applications. At least some embodiments of the disclosed functionalization methods are capable of providing functionalized ZnO or ZnO alloy films having improved electronic properties, including relatively high values of the conductivity and electron mobility, without resorting to any high temperature post-deposition steps. Since neither vacuum-based methods nor high-temperature post-deposition steps are required to achieve the desired electronic properties, at least some embodiments of the functionalized ZnO or ZnO alloy films may be produced more cheaply and efficiently. In addition, functionalized ZnO or ZnO alloy films may be formed over flexible substrates (e.g., polyethylene terephtalate (PET), polyethylene naphtalate (PEN), and paper), which are mechanically and chemically unstable at elevated temperatures, e.g., above about 200° C. Finally, the disclosed functionalization methods are compatible with the roll-to-roll processing techniques desirable for manufacturing large-area electronics on flexible substrates.

Functionalized ZnO or ZnO Alloy Films

The functionalized films comprise a film of ZnO or an alloy thereof disposed over a supporting substrate and a layer of organic molecules comprising terminal carboxylic acid linkage groups, wherein the organic molecules are bound to a surface of the film of ZnO or alloy thereof via the terminal carboxylic acid linkage groups. The components of the functionalized films, the ZnO or ZnO alloy films, the organic molecules and the supporting substrates, are described below.

Films of ZnO or ZnO Alloy

The films to be functionalized are films of ZnO or films of an alloy of ZnO. A variety of ZnO alloys may be used, including MgZnO and ZnSnO. The ZnO or alloy thereof may be undoped or doped, e.g., doped with Al, Mg, Ga, In, Cl or I. In some embodiments, the films consist of, or consist essentially of, ZnO. In some embodiments, the films consist of, or consist essentially of, an alloy of ZnO.

The film of ZnO or alloy thereof may be in contact with the underlying supporting substrate, e.g., in contact with the underlying supporting substrate along substantially the entire length of the film. The film of ZnO or alloy thereof may be a continuous film. The term "continuous" may be used to distinguish films formed of nanostructured ZnO or ZnO alloys, including films formed of a collection of discrete nanoparticles, which necessarily comprise gaps, channels, interstices, pores, etc. separating the nanostructures making up the film. In some embodiments, the film of ZnO or alloy thereof does not comprise, and is not composed of, nanostructured ZnO or ZnO alloys, e.g., a collection of discrete nanoparticles such as nanowires, nanorods, nanotubes, nanobelts, nanotetrapods, etc. In some embodiments, the film of ZnO or alloy thereof is not a nanoparticle, e.g., a nanowire, a nanorod, a nanotube, a nanobelt, or a nanotetrapod. In some embodiments, the film of ZnO or alloy thereof does not comprise, and is not composed of, mesoporous ZnO or ZnO alloy.

The films of ZnO or ZnO alloy to be functionalized by the disclosed methods may be characterized by their crystal structure. In some embodiments, the film of ZnO or alloy thereof is polycrystalline.

The films of ZnO or alloy thereof to be functionalized by the disclosed methods may be characterized by their dimensions. In some embodiments, the films of ZnO or alloy thereof are characterized by a thickness sufficient for the films to be incorporated as a transparent electrode in an optoelectronic device. In some embodiments, the films of ZnO or alloy thereof are characterized by a thickness sufficient for the films to be incorporated as the channel in a thin film transistor. In some embodiments, the films of ZnO or alloy thereof are characterized by a thickness of about 100 nm or less. This includes embodiments in which the thickness is about 75 nm or less, about 50 nm or less, or about 25 nm or less. This also includes embodiments in which the thickness is in the range of about 10 nm to about 100 nm, about 10 nm to about 75 nm, or about 10 nm to about 50 nm. The films of ZnO or alloy thereof may be substantially uniform such that the thickness of the film varies by no more than about ±20 nm. This includes embodiments in which the thickness of the film varies by no more than about ±10 nm, no more than about ±5 nm, or no more than about ±2 nm.

The other dimensions of the films of ZnO or alloy thereof, e.g., the length and the width for rectangular films, are not particularly limiting and can also depend upon the particular device and application for which the functionalized film is to be used. Films of ZnO or alloy thereof having lengths and/or widths of about 1 μm, 10 μm, 100 μm, 1 mm, 1 cm or even greater may be used. By way of example only, the scale of the length and/or width of the active channel area in a thin film transistor driving a typical active-matrix organic light-emitting diode (OLED) pixel may be in the range of about 5 μm to about 25 μm, with arrays of the thin film transistors covering large areas on the scale of cm to meters. As another example, the scale of the length and/or width of transparent electrodes for photovoltaics applications may be in the range of about 1 mm to about 1 m. Individual transparent electrodes may be combined with metal wire interconnects to cover larger areas. The films of ZnO or ZnO alloy may also be characterized by the ratio of their width-to-thickness. In some embodiments, the ratio of the width-to-thickness is about 10 or greater. This includes embodiments in which the ratio of the width-to-thickness is about 20 or greater, about 30 or greater, about 40 or greater, about 50 or greater, or about 100 or greater. The "width" may refer to the second-largest cross-sectional dimension of the film whereas the "length" may refer to the largest cross-sectional dimension of the film. The films of ZnO or alloy thereof may assume other shapes, e.g., circular films. Circular films may be characterized as having diameters and ratios of diameter-to-thickness with the ranges of the widths and ratios of width-to-thickness above. The films of ZnO or alloy thereof need not be symmetric in which case the "width" of such films may refer to the second-largest cross-sectional dimension of the film.

As noted above, in some embodiments, solution-based methods are used to form the films of ZnO or alloy thereof to be functionalized by the disclosed methods. A suitable sol-gel processing method is described in the Examples, below. Films of ZnO or alloy thereof formed by this and other solution-based methods may be referred to as "solution-deposited" films. Such solution-deposited films of ZnO or alloy thereof may be distinguished from films formed by vacuum-based methods, e.g., by the small size of individual crystals, the high the density of defects and/or impurities in the solution-deposited films. However, the disclosed functionalization methods are not limited to solution-deposited films. Thus, in some embodiments, vacuum-based methods are used to form the films of ZnO or alloy thereof to be functionalized by the disclosed methods.

In some embodiments, the films of ZnO or alloy thereof to be functionalized by the disclosed methods have not been subjected to high temperature post-deposition steps, such as high temperature annealing in hydrogen-rich or oxygen-rich environments. Films of ZnO or alloy thereof that have not been subjected to such high temperature post-deposition steps may be referred to as "as-deposited" films. Such as-deposited films of ZnO or alloy thereof may be distinguished from films subjected to high temperature post-deposition steps by the concentration of charge carriers.

Organic Molecules

The functionalized films comprise a layer of organic molecules comprising terminal carboxylic acid linkage groups. These organic molecules, bound to a surface of the film of ZnO or alloy thereof via the terminal carboxylic acid linkage groups, are derivatives of precursor organic molecules comprising terminal carboxylic acid (COOH) groups. These terminal carboxylic acid groups bind (e.g., via a covalent bond) to a surface of the film of ZnO or alloy thereof, which may transform the carboxylic acid group into a derivative group (i.e., the carboxylic acid linkage group), such as a carboxylate group ($COO^-$). Thus, the layer of organic molecules comprising terminal carboxylic acid linkage groups, wherein the organic molecules are bound to a surface of the film of ZnO or alloy thereof via the terminal carboxylic acid linkage groups, encompasses the reaction product of precursor organic molecules comprising terminal carboxylic acid groups with the surface of the film of ZnO or alloy thereof, including reaction products in which the carboxylic acid groups have been transformed into derivative groups.

A variety of organic molecules comprising terminal carboxylic acid linkage groups may be used. In some embodiments, the organic molecule is one which is capable of providing the functionalized film with a desired conductivity or electron mobility, including conductivities or electron mobilities within the ranges described below. In some embodiments, the organic molecules comprise, consist essentially of, or consist of derivatives of saturated fatty acids or derivatives of unsaturated fatty acids. In some embodiments, the organic molecules comprise, consist essentially of, or consist of derivatives of molecules having the formula $CH_3—(CH_2)_n—COOH$, where n is an integer from 1 to 24. Combinations of different organic molecules may be used. Specific, suitable organic molecules include derivatives of myristic acid, derivatives of palmitic acid, derivatives of stearic acid and derivatives of arachidic acid. These fatty acids may be unsubstituted or substituted, e.g., with fluorine. Other suitable organic molecules include derivatives of pyridine carboxylic acids, including derivatives of bipyridine carboxylic acids. Other suitable organic molecules include derivatives of thiophene carboxylic acids, derivatives of phenyl carboxylic acids and derivatives of thienyl carboxylic acids. In some embodiments, the organic molecules comprise, consist essentially of, or consist of any of these specific organic molecules or combinations thereof. As described above, by "derivative" it is meant the reaction product of the precursor organic molecule comprising a terminal carboxylic acid group with the surface of the film of ZnO or alloy thereof. For example, stearic acid is a precursor organic molecule which becomes a derivative of stearic acid (i.e., an organic molecule comprising a terminal carboxylic acid linkage group) once bound to a surface of a film of ZnO or alloy thereof.

In some embodiments, the organic molecules do not comprise derivatives of photosensitizing dye molecules.

Functionalized ZnO or ZnO alloy films having various surface coverages of organic molecules comprising terminal carboxylic acid linkage groups may be used. In some embodiments, the surface coverage of organic molecules is sufficient to provide the functionalized ZnO or ZnO alloy film with a desired conductivity or electron mobility, including conductivities and electron mobilities within the ranges described below. In some embodiments, the functionalized ZnO or ZnO alloy films comprise a monolayer of organic molecules comprising terminal carboxylic acid linkage groups. In some embodiments, the functionalized ZnO or ZnO alloy films comprise only a single monolayer (i.e., no more than one monolayer) of organic molecules comprising terminal carboxylic acid linkage groups. However, the functionalized ZnO or ZnO alloy films may comprise regions which are functionalized with the disclosed organic molecules comprising terminal carboxylic acid linkage groups and regions which are unfunctionalized, such that the unfunctionalized regions are substantially free of organic molecules comprising terminal carboxylic acid linkage groups.

The films of ZnO or alloy thereof may be deposited on a variety of supporting substrates, including silicon and glass. Flexible, supporting substrates may be used, including polyethylene terephthalate (PET), polyethylene naphthalate (PEN), paper and other similar polymeric materials.

The functionalized ZnO or ZnO alloy films may be characterized by their electronic properties, including saturation electron mobility. In some embodiments, the functionalized ZnO or ZnO alloy film exhibits a saturation electron mobility that is at least about 2 times greater than the saturation electron mobility of the unfunctionalized film, i.e., the ZnO or ZnO alloy film substantially free of the organic molecules comprising terminal carboxylic acid linkage groups. This includes embodiments in which the functionalized ZnO or ZnO alloy film exhibits a saturation electron mobility that is at least about 5 times, at least about 7 times, at least about 10 times, at least about 15 times, or at least about 20 times greater than the saturation electron mobility of the unfunctionalized film. This also includes embodiments in which the functionalized ZnO or ZnO alloy film exhibits a saturation electron mobility that is in the range of about 2 times to about 20 times greater than the saturation electron mobility of the unfunctionalized film. The saturation electron mobility may be referred to as the in-plane mobility or the field-effect mobility. The saturation electron mobility may refer to the mobility at room temperature.

Similarly, the functionalized ZnO or ZnO alloy films may be characterized by their conductivity. In some embodiments, the functionalized ZnO or ZnO alloy film exhibits a conductivity that is at least about 2 times greater than the conductivity of the unfunctionalized film, i.e., the ZnO or ZnO alloy film substantially free of the organic molecules comprising terminal carboxylic acid linkage groups. This includes embodiments in which the functionalized ZnO or ZnO alloy film exhibits a conductivity that is at least about 5 times, at least about 7 times, at least about 10 times, at least about 15 times, or at least about 20 times greater than the conductivity of the unfunctionalized film. This also includes embodiments in which the functionalized ZnO or ZnO alloy film exhibits a conductivity that is in the range of about 2 times to about 20 times greater than the conductivity of the unfunctionalized film. The conductivity may be referred to as the zero-gate bias conductivity or the zero-bias conductivity. The conductivity may refer to the conductivity at room temperature. The conductivity may be reported as the corresponding effective resistivity.

Devices

The functionalized ZnO or ZnO alloy films may be incorporated into a variety of devices. An exemplary device is a thin film transistor. As used herein, the "thin film transistor" may also be referred to as a field-effect transistor (FET). In some embodiments, the thin film transistor comprises a layer of a gate material; a layer of a dielectric material disposed over and in contact with the layer of the gate material; a functionalized ZnO or ZnO alloy film disposed over and in contact with the layer of the dielectric material; a source disposed over the layer of the dielectric material and in contact with the functionalized ZnO or ZnO alloy film; and a drain disposed over the layer of the dielectric material and in contact with the functionalized ZnO or ZnO alloy film. The configuration of the source and drain with respect to the layer of the dielectric material may vary. In a one configuration, the source and drain are each in contact with the functionalized ZnO or ZnO alloy film, but are not in contact with the layer of the dielectric material. An exemplary such embodiment is shown in FIG. 1B. The thin film transistor 100 includes a layer of a gate material 102; a layer of a dielectric material 104; a functionalized ZnO film comprising a film of ZnO 106 and a monolayer 107 of organic molecules comprising terminal carboxylic acid linkage groups bound to a surface of the film of ZnO via the terminal carboxylic acid linkage groups; a source 108; and a drain 110. In another configuration, the source and the drain are each in contact with the functionalized ZnO or ZnO alloy film and the layer of the dielectric material. For example, the source and drain may be deposited on the layer of the dielectric material and the functionalized ZnO or ZnO alloy film may be formed over the source, the drain, and the layer of the dielectric material.

In the above description of the thin film transistor, the term "over" is not meant to be limited to a particular direction. Rather, the layer of the gate material may be defined as the bottom-most layer such that the disclosed thin film transistors encompass bottom-gate thin film transistors. However, the layer of the gate material may be defined as the top-most layer such that the disclosed thin film transistors also encompass top-gate thin film transistors.

Materials for the dielectric material, the gate material, the source and the drain are known. Any of the disclosed functionalized ZnO or ZnO alloy films may be used. The thin film transistors may be formed on a variety of supporting substrates, including the supporting substrates disclosed herein.

In some embodiments of the thin film transistors, the interface formed between the source and the functionalized ZnO or ZnO alloy film and the interface formed between the drain and the functionalized film each are substantially free of the organic molecules comprising terminal carboxylic acid linkage groups. In other words, in such embodiments, the functionalized ZnO or ZnO alloy film comprises a first unfunctionalized region at the interface formed with the drain and a second unfunctionalized region at the interface formed with the source. FIG. 1B shows an exemplary embodiment of such a thin film transistor. The Examples below show that despite the absence of the organic molecules at the source/drain interfaces, the functionalized ZnO films exhibit increased conductivity and electron mobility.

The functionalized ZnO or ZnO alloy films and/or the thin film transistors comprising the functionalized films may be incorporated into a variety of optoelectronic devices. One class of optoelectronic devices includes flat panel displays, e.g., organic light-emitting diode (OLED) displays. The disclosed functionalized ZnO or ZnO alloy films may be used as the transparent electrode(s) in such devices. The disclosed thin film transistors may be used to drive the pixels in such displays. By way of example only, an embodiment of an OLED comprises any of the disclosed functionalized ZnO or ZnO alloy films, a counter electrode, and a film of electroluminescent organic molecules disposed between the functionalized ZnO or ZnO alloy film and the counter electrode. Such OLEDs may be organized in an array. As another example, an embodiment of an OLED display comprises a backplane comprising an array of any of the disclosed thin film transistors disposed over a substrate and an array of OLEDs disposed over the backplane, wherein the OLEDs are in electrical communication with the thin film transistors. A second class of optoelectronic devices includes large-area lighting panels, in which the disclosed functionalized ZnO or ZnO alloy films are used as the transparent electrode. By way of example only, an embodiment of a large-area lighting panel comprises any of the disclosed functionalized ZnO or ZnO alloy films in contact with a blend(s) of electroluminescent and/or phosphorescent organic molecules. In such lighting panels, the functionalized film is electrically and optically uniform over large areas on the scale of from cm to meters.

Another class of optoelectronic devices includes photovoltaic devices, e.g., thin film solar cells. The functionalized ZnO or ZnO alloy films may be used as the transparent electrode(s) in such devices. A variety of thin film solar cells may be used. By way of example only, a photovoltaic device comprises an electrode, a p-type absorber layer disposed over the electrode, an n-type layer disposed over the p-type absorber layer and any of the disclosed functionalized ZnO or ZnO alloy films disposed over the n-type layer.

Sensors for detecting carboxylic acid group-containing molecules, e.g., from liquid samples suspected of containing carboxylic acid group-containing molecules, are also provided. In some embodiments, a sensor comprises a thin film transistor comprising a layer of a gate material; a layer of a dielectric material disposed over and in contact with the layer of the gate material; a ZnO or ZnO alloy film disposed over and in contact with the layer of the dielectric material; a source disposed over the layer of the dielectric material and in contact with the ZnO or ZnO alloy film; and a drain disposed over the layer of the dielectric material and in contact with the ZnO or ZnO alloy film. As with the thin film transistors disclosed above, the configuration of the source and drain with respect to the layer of the dielectric material may vary and the term "over" is not meant to be limited to a particular direction. In some embodiments of the sensors, the interface formed between the source and the ZnO or ZnO alloy film and the interface formed between the drain and the ZnO or ZnO alloy film each are buried interfaces such that they are substantially inaccessible by any of the carboxylic acid group-containing molecules that may come into contact with the ZnO or ZnO alloy film. Any of the disclosed ZnO or ZnO alloy films may be used. The disclosed sensors are capable of detecting carboxylic acid group-containing molecules in a sample in contact with the ZnO or ZnO alloy film by an increase in conductivity or electron mobility of the film as the carboxylic acid groups bind to the surface of the film. As such, at least initially, the ZnO or ZnO alloy film of the sensor may be unfunctionalized. As further discussed below, the sensor can be exposed to an environment or sample in which carboxylic acids may be present and can be used to report the concentration of such molecules. Following use, the sensors can be "reset" to their initial (unfunctionalized) states by removing the bound carboxylic acid groups. A variety of techniques may be used to remove the bound carboxylic acid groups, including an ultraviolet/ozone process of the type described below.

The sensors further comprise a device configured to measure the electron mobility or the conductivity of the ZnO or ZnO alloy film in the presence of a sample in contact with the film. Such devices may include a power source configured to apply a voltage to the layer of the gate material, an ammeter configured to measure the drain current as a function of gate voltage and a processor configured to calculate the electron mobility from a plot of the drain current versus gate voltage. Such devices may include a power source configured to apply a voltage to the layer of the gate material, an ammeter configured to measure the drain current as a function of drain voltage and a processor configured to calculate the conductivity from a plot of the drain current versus drain voltage. The device, e.g., the processor of the device, may also be configured to indicate (e.g., via a visual or audio signal) the presence or absence of carboxylic acid group-containing molecules in a sample in contact with the ZnO or ZnO alloy film from the measured conductivity or electron mobility. The device, e.g., the processor of the device, may also be configured to determine the concentration of carboxylic acid group-containing molecules in a sample in contact with the ZnO or ZnO alloy film from the measured conductivity or electron mobility, e.g., by comparison to a calibration curve. The carboxylic acid group-containing molecules that may be detected by the sensors include any of the precursor organic molecules disclosed above. However, the types of carboxylic acid group-containing molecules that may be detected is not particularly limiting, provided the molecules bind to the surface of the ZnO or ZnO alloy films of the sensors and provide a measurable increase in conductivity or electron mobility of the film.

Methods

Methods of forming the functionalized ZnO or ZnO alloy films are provided which comprise exposing a ZnO or ZnO alloy film to a solution comprising precursor organic molecules comprising terminal carboxylic acid groups and an organic solvent, whereby the precursor organic molecules bind to the surface of the ZnO or ZnO alloy film via the terminal carboxylic acid groups to provide a layer of organic molecules comprising terminal carboxylic acid linkage groups bound to the surface of the film of ZnO or ZnO alloy. The methods may further comprise measuring the conductivity or electron mobility of the functionalized ZnO or ZnO alloy film, e.g., to determine if a desired conductivity or electron mobility has been achieved. Any of the precursor organic molecules described above may be used. Any of the ZnO or ZnO alloy films described above may be used (e.g., a solution-processed, as-deposited ZnO film). The functionalization may be carried out at various temperatures (e.g., room temperature) and times (e.g., a few hours) in order to achieve desired surface coverages. Similarly, various concentrations of the precursor organic molecules comprising terminal carboxylic acid groups in the solution may be used.

Although a variety of organic solvents may be used in the methods, in general, the organic solvent is selected to minimize the etching of the ZnO or ZnO alloy film during functionalization. The suitability of an organic solvent can depend upon the particular precursor organic molecule selected for functionalization. The suitability of an organic solvent can also depend upon the thickness of the ZnO or ZnO alloy film to be functionalized and the length of time used for the functionalization. By way of explanation, the acid dissociation constant (Ka) for carboxylic acids can depend upon the organic solvent used to dissolve the carboxylic acid. More specifically, the acid dissociation constant (Ka) is smaller (pKa larger) for carboxylic acids in THF than in certain other solvents. Higher pKa corresponds to less acidic solutions, which etch the ZnO or ZnO alloy surface more slowly. Values of pKa for acetic acid, a simple molecule with a carboxylic acid group, in various solvents are summarized in the table below. The values of pKa for acetic acid provide insight into what can be expected with more complex carboxylic acids. The table also illustrates the expected correlation of pKa with the relative dielectric constant $\in_r$ of the solvent, and gives the H$^+$ ion concentrations in solutions composed of the various solvents. The expected concentration of dissociated hydrogen ions is more than 5 orders of magnitude lower in THF than in ethanol, dimethyl sulfoxide (DMSO), or dimethylformamide (DMF). In fact, the pKa is sufficiently high in THF that ZnO or ZnO alloy films with nanometer thicknesses can be immersed in THF/carboxylic acid solutions for as long as three days with substantially no etching of the ZnO or ZnO alloy surface apparent in optical microscopy or atomic force microscopy. By contrast, the same concentration of the carboxylic acid in ethanol, DMSO or DMF can completely dissolve the ZnO or ZnO alloy film in the same period of time. In some embodiments, the organic solvent is selected to result in substantially no etching of the ZnO or ZnO alloy film at room temperature over a period of about three days.

TABLE

The pKa, hydrogen ion concentration, molecular dipole moment and dielectric constant for various solvents for functionalizing ZnO or ZnO alloy films.

| solvent | pKa (acetic acid) | [H$^+$] for 1 mM acetic acid (M) | dipole moment (D) | $\in_r$ |
|---|---|---|---|---|
| H$_2$O | 4.76 | $1 \times 10^{-4}$ | 1.85 | 80 |
| methanol | 9.7 | $4 \times 10^{-7}$ | 1.70 | 33 |
| ethanol | 10.3 | $2 \times 10^{-7}$ | 1.69 | 24 |
| DMSO | 12.6 | $2 \times 10^{-8}$ | 3.96 | 49 |
| DMF | 13.5 | $6 \times 10^{-9}$ | 3.86 | 37 |
| acetonitrile | 22.3 | $2 \times 10^{-13}$ | 3.92 | 36 |
| THF | 24 | $3 \times 10^{-14}$ | 1.75 | 7.6 |

The pKa and dielectric constants are from F. Ding, J. M. Smith, and H. Wang, J. Org. Chem. 74, 2679 (2009) for acetonitrile and THF, and from T. W. G. Solomons and C. B. Fryhle, Organic Chemistry, 247 (Wiley, 2008) for other solvents. The pKa are taken from K. Sarmini and E. Kenddler, J. Biochem. Biophys. Methods 38, 123 (1999) for DMSO and DMF and from F. Maran, D. Celadon, M. G. Severin, and E. Vianello, J. Am. Chem. Soc. 113, 9320 (1991) for other solvents. The dipole moments are from F. Maran, D. Celadon, M. G. Severin, and E. Vianello, J. Am. Chem. Soc. 113, 9320 (1991).

Methods for using the disclosed sensors to detect carboxylic acid group-containing molecules are also provided. The methods comprise exposing the ZnO or ZnO alloy film of any of the disclosed sensors to a sample and measuring the conductivity or electron mobility of the ZnO or ZnO alloy film, whereby the measured conductivity or electron mobility indicates the presence or absence of carboxylic acid group-containing molecules in the sample. For example, an increase in the electron mobility of the ZnO or ZnO alloy film indicates the presence of carboxylic acid group-containing molecules in the sample, whereas an unchanged electron mobility indicates the absence of carboxylic acid-group containing molecules. The methods may further comprise determining the concentration of the carboxylic acid group-containing molecules in the sample from the measured conductivity or electron mobility. The methods may further comprise removing the organic molecules comprising terminal carboxylic acid linkage groups from a surface of the ZnO or ZnO alloy film. By way of example, the methods may further comprise exposing the ZnO or ZnO alloy film to a source of ultraviolet radiation and ozone, whereby organic molecules comprising terminal carboxylic acid linkage groups are removed from a surface of the ZnO or ZnO alloy film.

The functionalized ZnO or ZnO alloy films, related devices and methods will be understood more readily by reference to the following examples, which are provided by way of illustration and are not intended to be limiting.

EXAMPLES

As shown in FIG. 1A, ZnO films 106 were deposited by spin coating a precursor solution onto substrates consisting of 300 nm $SiO_2$ on highly doped silicon, which served as the gate dielectric 104 and bottom gate 102, respectively. The precursor solution consisted of 0.3 M zinc acetate dihydrate in absolute ethanol with 0.3 M of acetylacetone added as a stabilizer. The precursor solution was stirred overnight at room temperature and filtered through a 0.2 μm polytetrafluoroethylene filter prior to spin coating. The substrates were pre-cleaned in a 3:1 mixture of sulfuric acid and hydrogen peroxide for 5 minutes, which was heated to approximately 80° C. by the exothermic reaction that occurs upon mixing the solution. The substrates were then sonicated for 5 minutes each in acetone, isopropyl alcohol, and water. The ZnO precursor was deposited onto the $SiO_2$ by spin coating at 5000 revolutions per minute for 30 seconds followed by heating to 75° C. for 10 minutes to evaporate residual solvent. The coating process was then repeated. The films were annealed in air in a quartz tube furnace at 450° C. for 75 minutes to convert the ZnO precursor to polycrystalline ZnO. The processing steps did not include exposure to a high-temperature hydrogen gas environment.

Source 108 and drain 110 top contacts were formed by depositing Al films with a thickness of 100 nm by electron-beam evaporation through a shadow mask with channel lengths and width of 100 μm and 1000 μm, respectively. The ZnO exhibited a crystallographic texture in which the c-axis was along the surface normal of the substrate. X-ray diffraction 0-20 scans over an angular range in which the ZnO [100], [002], [101], and [102] reflections would occur exhibit only the [002] reflection.

A self-assembled monolayer 107 of stearic acid was added to the ZnO surface by immersing the ZnO FETs in a 1 mM solution of stearic acid in tetrahydrofuran (THF) at room temperature for 2 hours. The FET 100 with the functionalized ZnO film is shown in FIG. 1B.

Figure 2:
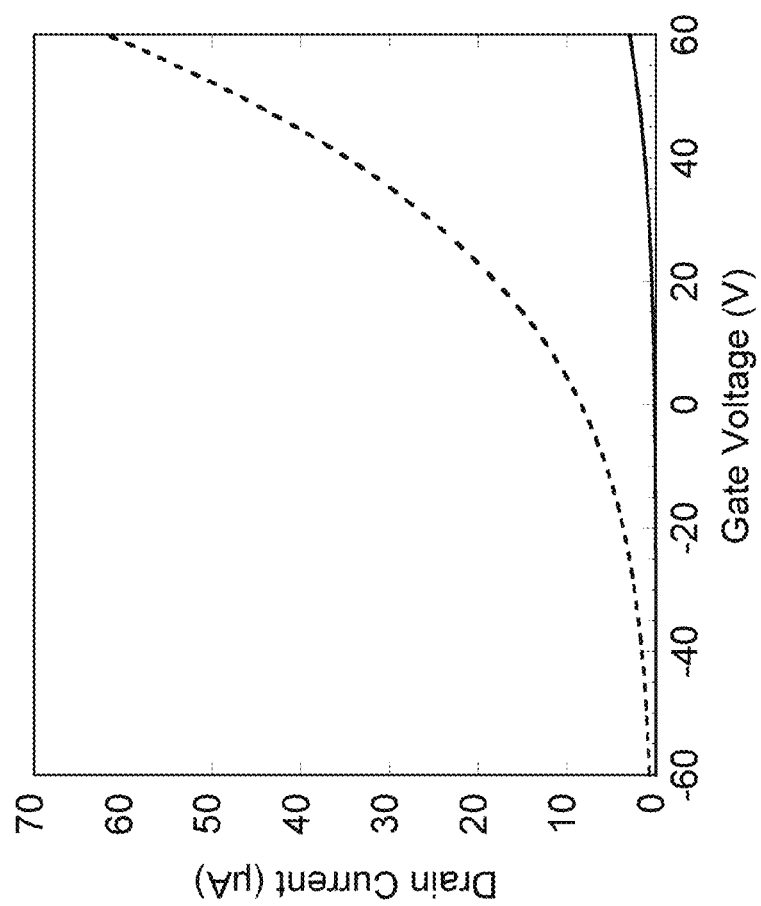
FIG. 2 shows the drain current as a function of gate voltage for a FET comprising an unfunctionalized ZnO film (solid curve) and for the same device after functionalization of the ZnO film with stearic acid (dashed curve).
Figure 3B:
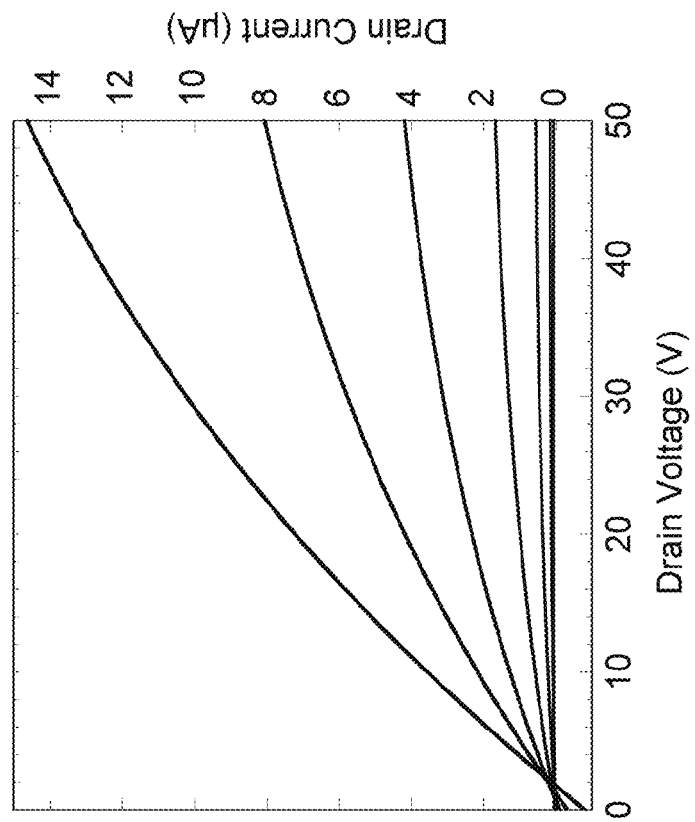
FIG. 3 shows the output characteristics of a ZnO FET before (A) and after (B) functionalization of the ZnO film with stearic acid. The gate voltage increases in steps of 20 V from −60 V (off) to +60 V (on).
Figure 3A:
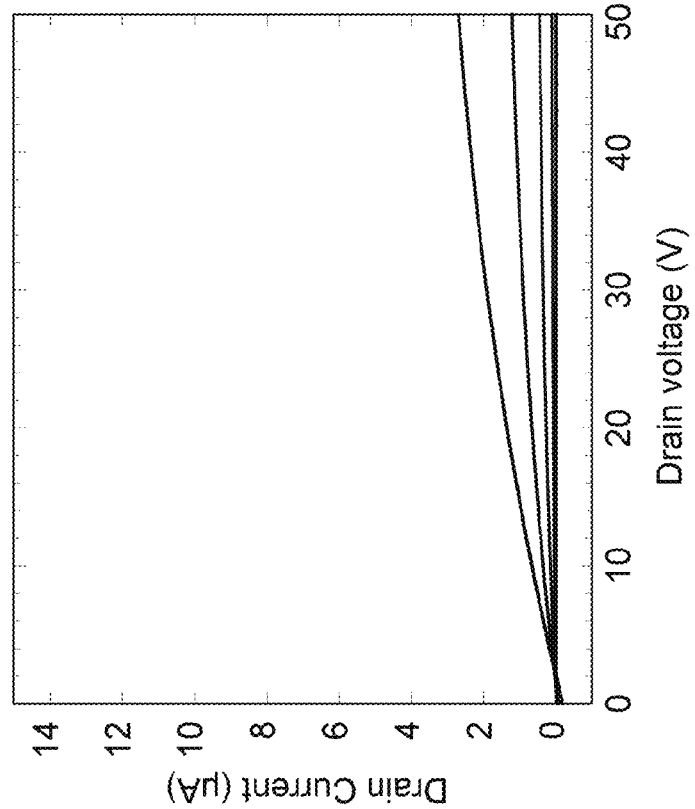

FIG. 2 shows the drain current as a function of gate voltage for a ZnO FET before (solid curve) and after (dashed curve) the creation of the stearic acid layer. The saturation electron mobility increases from 0.01 $cm^2$ $V^{-1}$ $s^{-1}$ in the as-deposited FET to 0.13 $cm^2$ $V^{-1}$ $s^{-1}$ after attachment of stearic acid to the surface. FIGS. 3A-B show the output characteristics, in which the drain current is measured as a function of drain voltage $V_d$ at a series of different gate voltages, for a representative transistor before (A) and after (B) functionalization with stearic acid. In addition to the increased source-drain current after stearic acid functionalization, FIG. 3B also exhibits a small non-zero current at $V_d=0$, arising from the gate leakage at high gate voltages. Electrical measurements were made in the dark in order to eliminate possible contributions to the source-drain current due to photocurrent or a light-induced threshold voltage shift.

The zero gate bias conductivity was extracted from measurements of the conductance using the slope of the $I_d$ versus $V_d$ plots in FIGS. 3A-B. The slopes were measured in the linear region of transistor operation, with $V_d<10$ V. The conductivity was calculated from the conductance assuming that the electrons responsible for conduction are uniformly distributed throughout the 25 nm thick ZnO film. The corresponding effective resistivity of the channel decreased by an order of magnitude from an initial value of $4.5\times10^3$ Ωcm to $4.2\times10^2$ Ωcm after functionalization with the stearic acid monolayer. Undoped ZnO layers with thicknesses less than 50 nm typically have very high resistivities of more than $10^3$ Ωcm. Introducing the stearic acid layer yields undoped ZnO films with resistivities of equal magnitude to what can be achieved by doping or by annealing in hydrogen.

Figure 4:
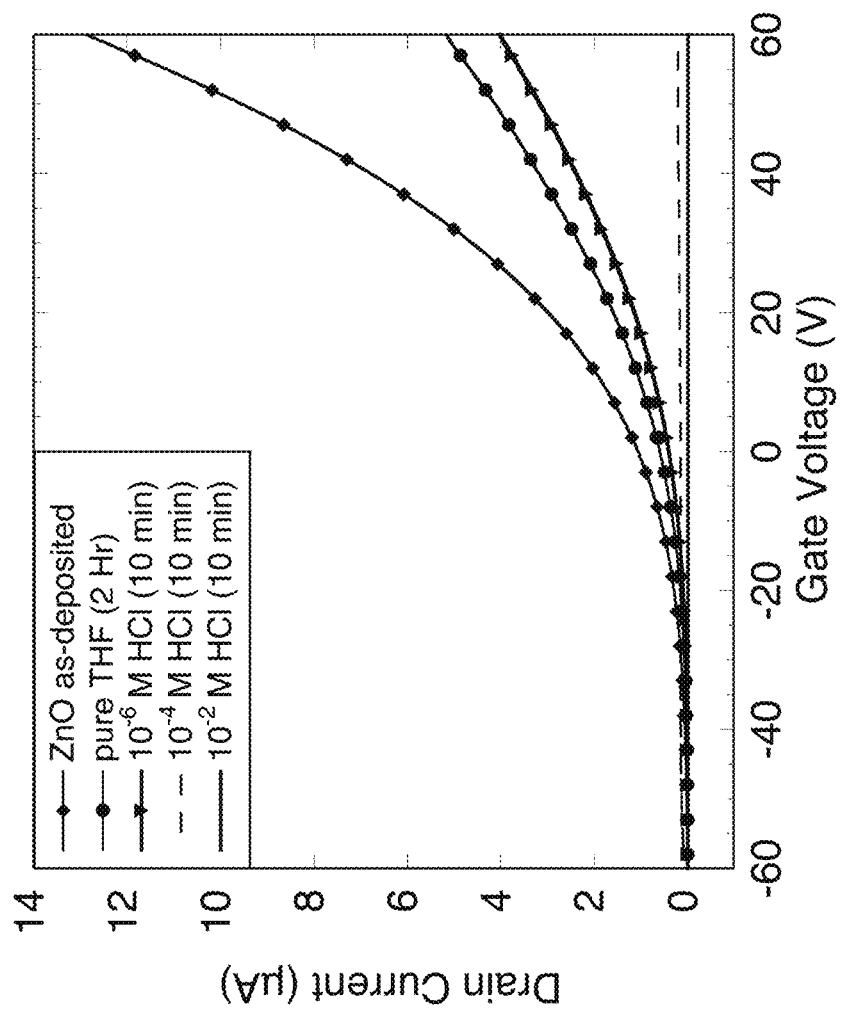
FIG. 4 shows drain current as a function of gate voltage for a ZnO FET after etching in dilute solutions of HCl in THF. The as-deposited ZnO FET (diamonds) has the highest current. The source-drain current decreases after immersion in pure THF for 2 hours (circles) and continues to decrease after 10 minutes immersion in solutions of HCl in THF with concentrations of $10^{-6}$ M (triangles) and $10^{-4}$ M (dashed line). The ZnO channel is completely removed after 10 minutes in a solution of $10^{-2}$ M HCl in THF (solid line).

Mechanisms that could potentially contribute to the increased electron mobility include (1) etching of the ZnO surface eliminating defects that would increase electron scattering and therefore decrease carrier mobility, (2) passivation of defect scattering sites by covalent bonding of the carboxylic acid groups to defects, resulting in direct chemical passivation and/or a beneficial local electric field, and (3) the incorporation of the hydrogen released from the carboxylic acid group into the ZnO film, accompanied by some reductive process, where H could act as a dopant. To investigate the possibility that the increased mobility results from etching that eliminates surface defects, a control experiment was performed in which ZnO FETs were subjected to treatments in a dilute inorganic acid to etch the surface. A ZnO FET was immersed in increasingly acidic HCl solutions for 10 minutes, rinsed with clean THF, and dried with a nitrogen gun. Hydrochloric acid was selected for the control experiments because, unlike stearic acid, the $Cl^-$ anion in HCl does not covalently bind to the ZnO surface in the same manner as a carboxylic acid group. The drain current was measured as a function of gate voltage between each immersion step in the etching experiment. As shown in FIG. 4, mild etching of ZnO film with the dilute HCl solutions consistently decreased the conductivity of the films. This etching experiment exhibits the opposite effect as is found in the case of carboxylic acid surface functionalization, thus eliminating the possibility that etching contributes to the improvement of the mobility.

If the electronic effect on the ZnO is due to the carboxylic acid binding chemistry, rather than physical changes to the ZnO structure by etching, or incorporation of hydrogen atoms into the ZnO lattice, it should be reversible by removing the organic molecules from the surface. To investigate the potential reversibility of the observed electronic effect, the FET structures were placed within 5 mm of an ozone-producing ultraviolet lamp after the stearic acid surface treatment. The combination of UV photons and ozone breaks C—C bonds in organic molecules and converts the molecular fragments to volatile species that leave the surface, comprising an effective room-temperature, dry cleaning method for removing organic surface molecules.

Figure 5A:
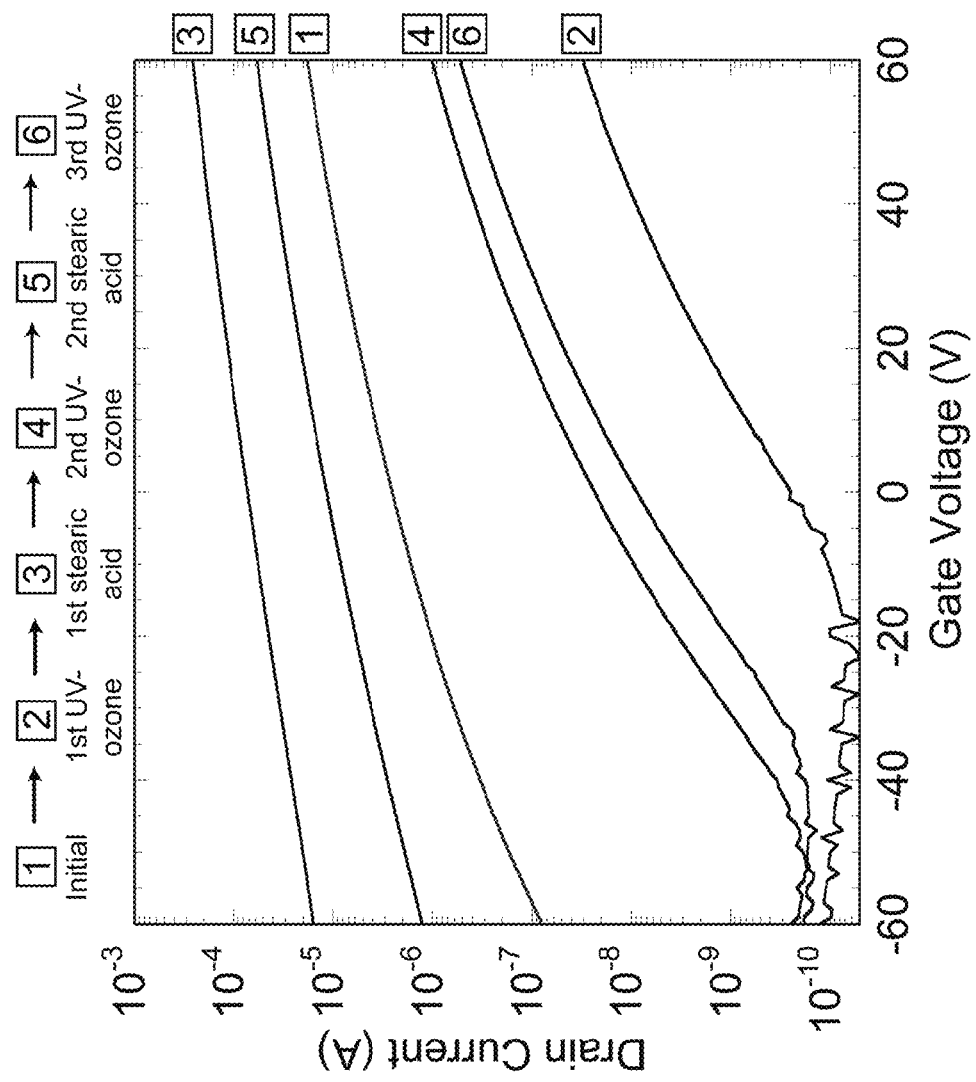
FIG. 5A shows transfer curves of a single ZnO FET device measured after alternating surface treatments of stearic acid and UV-ozone showing the reversibility of the carboxylic acid electronic effect. The numbered boxes indicate the sequence of the surface treatments.

The transfer characteristics of a ZnO FET device (FIG. 5A), and the drain current as a function of drain voltage at $V_g=0$ (FIG. 5B) were measured after sequentially alternating treatments of a single ZnO FET sample between a UV-ozone lamp and the stearic acid treatment. After each round of stearic acid treatment, the samples were found to be hydrophobic and after UV-ozone treatment the samples became hydrophilic, as observed by placing a drop of deionized water on the ZnO film surface. FIG. 5A shows the initial transfer characteristics of a ZnO FET sample, which had been stored in ambient conditions for several weeks (1), then exposed to a UV-ozone lamp for 5 minutes and re-measured within 5 minutes of the end of exposure (2). The FET was then functionalized following the previously described procedure in a 1 mmol stearic acid solution (3), and again exposed to the UV-ozone lamp for 5 minutes (4). The stearic acid and UV ozone treatments were then repeated once more each (5) & (6). The drain current at all gate voltages is several orders of magnitude higher for the ZnO FET when the stearic acid layer is present, compared to the device after it is exposed to UV-ozone.

Figure 5B:
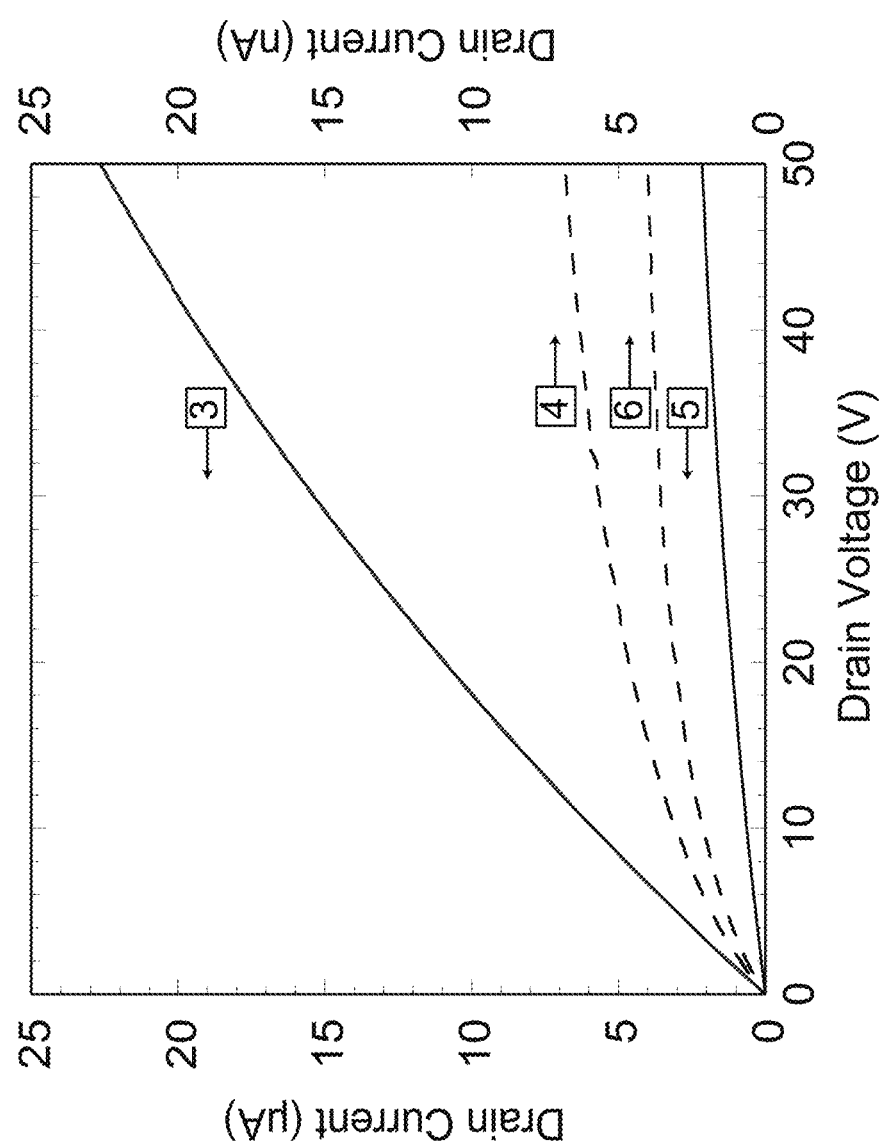
FIG. 5B shows the zero gate bias drain current as a function of drain voltage after alternating treatments with stearic acid (solid curves, left axis) and UV-ozone exposure (dashed curves, right axis). The scale for the left y-axis (μA) is a factor of $10^3$ larger than the right axis (nA).

FIG. 5B shows the drain current as a function of drain voltage at zero gate voltage for the sample after stearic acid treatments (solid curves, left y-axis), and after 5 minutes UV-ozone exposures (dashed curves, right y-axis). The resistivity of the ZnO functionalized with stearic acid, 43 $\Omega$cm, is increased by a factor of 2000 to $8.3\times10^4$ $\Omega$cm by removal of the surface layer with the UV-ozone treatment. It is noted that the resistivity of the ZnO devices with stearic acid was lowest if the film was first pre-treated with UV-ozone. This may be due to an increase in potential sites for carboxylic acid attachment that become available after the UV-ozone cleaning treatment.

The interaction between UV-ozone and the ZnO film is itself a complex process, and includes several competing effects such as the creation of additional oxygen interstitials or the removal of oxygen vacancies, both of which can reduce the ZnO conductivity with increasing UV-ozone dose, separate from the effects of removing the organic molecules from the surface. However, it can be concluded that the attachment of the organic layer is the dominant effect in restoring the high conductivity state, because the stearic acid solution treatment is not expected to significantly alter the concentrations of either oxygen vacancies or oxygen interstitials in the film.

Atomic force microscopy (AFM) images of the surface of the ZnO layer before the functionalization with stearic acid were obtained. The ZnO films comprised 25-75 nm diameter crystals. Line profiles extracted from the images indicated that the height of the surface varied over a range of less than 10 nm both before and after addition of the stearic acid layer and that there was no apparent change in the number density or diameter of the nanocrystals.

Similar experiments were carried out using bipyridine and Re1c ((2,2'-bipyridine-4-carboxylic acid)tricarbonylchlororhenium(I)) instead of stearic acid. A FET including a ZnO film functionalized with bipyridine exhibited a saturation electron mobility of about 0.11 cm$^2$ V$^{-1}$ s$^{-1}$. A FET including a ZnO film functionalized with Re1c exhibited a saturation electron mobility of about 0.12 cm$^2$ V$^{-1}$ s$^{-1}$.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like includes the number recited and refers to ranges which can be subsequently broken down into subranges as discussed above. Finally, as will be understood by one skilled in the art, a range includes each individual member.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A functionalized film comprising:
    a film of polycrystalline ZnO or alloy thereof disposed over a supporting substrate; and
    a layer of organic molecules comprising terminal carboxylic acid linkage groups, wherein the organic molecules are bound to a surface of the film of polycrystalline ZnO or alloy thereof via the terminal carboxylic acid linkage groups, wherein the surface is substantially unetched during functionalization to provide the functionalized film.

2. The functionalized film of claim 1, wherein the film of polycrystalline ZnO or alloy thereof is a continuous film.

3. The functionalized film of claim 1, wherein the film of polycrystalline ZnO or alloy thereof is not a nanobelt, a nanotetrapod, or a nanowire.

4. The functionalized film of claim 1, wherein the film of polycrystalline ZnO or alloy thereof is not mesoporous.

5. The functionalized film of claim 1, wherein the film of polycrystalline ZnO or alloy thereof is characterized by a thickness of about 100 nm or less and a ratio of width-to-thickness of about 20 or greater.

6. The functionalized film of claim 1, wherein the organic molecules comprise derivatives of saturated fatty acids.

7. The functionalized film of claim 1, wherein the organic molecules comprise derivatives of molecules having the formula $CH_3$—$(CH_2)_n$—COOH, where n is an integer from 1 to 24.

8. The functionalized film of claim 1, wherein the organic molecules comprise derivatives of stearic acid.

9. The functionalized film of claim 1, wherein the organic molecules comprise derivatives of pyridine carboxylic acids.

10. The functionalized film of claim 1, wherein the organic molecules do not comprise derivatives of photosensitizing dye molecules.

11. The functionalized film of claim 1, comprising a monolayer of the organic molecules.

12. The functionalized film of claim 1, wherein the supporting substrate is a flexible, polymeric substrate.

13. The functionalized film of claim 1, wherein the functionalized film exhibits a saturation electron mobility at room temperature of at least about 10 times greater than the saturation electron mobility of the unfunctionalized film.

14. The functionalized film of claim 1, wherein the film of polycrystalline ZnO or alloy thereof is characterized by a thickness of about 100 nm or less and further wherein the functionalized film exhibits a saturation electron mobility at room temperature of at least about 10 times greater than the saturation electron mobility of the unfunctionalized film.

15. The functionalized film of claim 14, comprising a monolayer of the organic molecules.

16. A thin film transistor comprising:
a layer of a gate material;
a layer of a dielectric material disposed over and in contact with the layer of gate material;
the functionalized film of claim 15 disposed over and in contact with the layer of the dielectric material;
a source disposed over the layer of the dielectric material and in contact with the functionalized film at a first interface; and
a drain disposed over the layer of the dielectric material and in contact with the functionalized film at a second interface.

17. A thin film transistor comprising:
a layer of a gate material;
a layer of a dielectric material disposed over and in contact with the layer of the gate material;
a functionalized film disposed over and in contact with the layer of the dielectric material, the functionalized film comprising:
a film of polycrystalline ZnO or alloy thereof, and
a layer of organic molecules comprising terminal carboxylic acid linkage groups, wherein the organic molecules are bound to a surface of the film of polycrystalline ZnO or alloy thereof via the terminal carboxylic acid linkage groups, wherein the surface is substantially unetched during functionalization to provide the functionalized film;
a source disposed over the layer of the dielectric material and in contact with the functionalized film at a first interface; and
a drain disposed over the layer of the dielectric material and in contact with the functionalized film at a second interface.

18. The thin film transistor of claim 17, wherein the first interface and the second interface are both substantially free of the organic molecules comprising terminal carboxylic acid linkage groups.

* * * * *